(12) United States Patent
Adams et al.

(10) Patent No.: US 8,034,037 B2
(45) Date of Patent: Oct. 11, 2011

(54) VACUUM WOUND DRESSING

(75) Inventors: Simon Adams, Holywell (GB); Stephen Bishop, Hawarden (GB); Bryan Griffiths, Chester (GB); Helen Shaw, Widnes (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 484 days.

(21) Appl. No.: 11/267,046

(22) Filed: Nov. 4, 2005

(65) Prior Publication Data
US 2006/0100594 A1 May 11, 2006

Related U.S. Application Data

(60) Provisional application No. 60/625,488, filed on Nov. 5, 2004.

(51) Int. Cl.
*A61M 1/00* (2006.01)
*A61M 27/00* (2006.01)
*A61M 35/00* (2006.01)
*A61F 13/00* (2006.01)

(52) U.S. Cl. .......... 604/313; 604/35; 604/289; 604/543; 604/304

(58) Field of Classification Search .................. 604/304, 604/35, 289, 290, 543, 313
See application file for complete search history.

(56) References Cited

U.S. PATENT DOCUMENTS

| 5,578,661 | A | * | 11/1996 | Fox et al. ..................... 524/27 |
| 5,636,643 | A | | 6/1997 | Argenta et al. |
| 5,643,187 | A | | 7/1997 | Naestoft et al. |
| 6,135,116 | A | | 10/2000 | Vogel et al. |
| 6,695,823 | B1 | | 2/2004 | Lina et al. |
| 6,767,334 | B1 | | 7/2004 | Randolph |

FOREIGN PATENT DOCUMENTS

| JP | 1-209072 | 8/1989 |
| WO | WO0061206 | 11/2000 |
| WO | WO03/092755 | 11/2003 |

* cited by examiner

*Primary Examiner* — Jaqueline F Stephens
(74) *Attorney, Agent, or Firm* — John M. Kilcoyne

(57) ABSTRACT

Provided, in one embodiment, is a vacuum wound dressing for covering a wound bed comprising: a wound contact layer comprising a fibrous blend or fibrous material that forms a cohesive gel when wetted by wound exudate; a source of vacuum situated to be separated from the wound bed by the wound contact layer; and a vacuum sealing layer covering the wound contact layer and adapted to retain relative vacuum in the wound contact layer, wherein (i) the dressing is essentially missing a non-gelling, foam layer in which the source of vacuum is situated or (ii) the vacuum sealing layer comprises as an outer layer a foam layer.

7 Claims, 3 Drawing Sheets

VACUUM WOUND DRESSING

This application claims the priority of U.S. Provisional Application No. 60/625,488, filed Nov. 5, 2004.

The present invention relates to methods, devices and kits for treating a wound with a dressing and vacuum.

Vacuum has been used to increase blood flow to wound tissue and to remove exudate from the wound site. It is believed that it has not been recognized that such methods can be effectively combined with gel-forming wound care products placed against the wound to which vacuum is applied.

SUMMARY OF THE INVENTION

Provided, in one embodiment, is a vacuum wound dressing for covering a wound bed comprising: a wound contact layer comprising a fibrous blend or fibrous material that forms a cohesive gel when wetted by wound exudate; a source of vacuum situated to be separated from the wound bed by the wound contact layer; and a vacuum sealing layer covering the wound contact layer and adapted to retain relative vacuum in the wound contact layer, wherein (i) the dressing is essentially missing a non-gelling, foam layer in which the source of vacuum is situated or (ii) the vacuum sealing layer comprises as an outer layer a foam layer.

Provided, in another embodiment, is a vacuum wound care module comprising: an fluid reservoir; a pump module fluidly connected to the irrigation reservoir and adapted for pumping fluid out of the fluid reservoir; a venturi vacuum fitting fluidly connected to the pump module and having a vacuum outlet and a fluid outlet; a fluid connection from the fluid outlet to the fluid reservoir; a trap reservoir fluidly connected to the vacuum outlet; and a second fluid connection that is (i) adapted to be fitted with a wound dressing to provide vacuum and allow removal of wound exudate or (ii) fitted to such a wound dressing such that, when the wound dressing is employed, it provides vacuum and allows removal of wound exudate.

DETAILED DESCRIPTION OF THE INVENTION

Figure 1A:
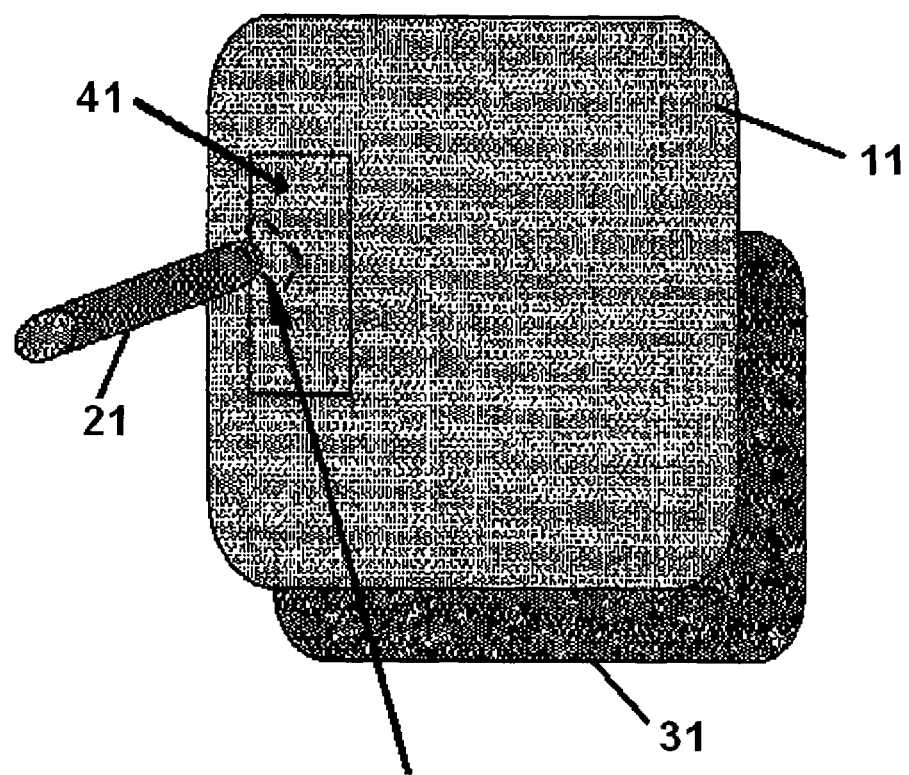
FIG. 1a shows a top view of separated products used in an illustrative embodiment of the invention.
Figure 1B:
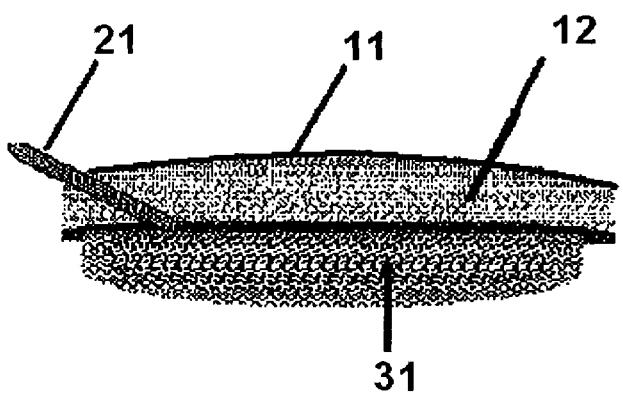
FIG. 1b shows a side view of the illustrative embodiment.

The outer dressing used in the vacuum method can include a vacuum sealing outer layer that is film layer 11, and a foam layer 12. As illustrated in FIGS. 1a and 1b, a vacuum source connector 21 (e.g., silicone tubing) can be slotted through film layer 11 and foam layer 12, and sealed with another adhesive film 41. Film 41 can be, for example, the Opsite™ film dressing from Smith & Nephew (Cambridge, United Kingdom). The vacuum permeable foam layer 12 is separated from direct contact with the wound by wound contact layer 31.

As illustrated, the source of vacuum (illustrated as tubing) is favorably separated from the wound by a wound contact layer, or a portion of a wound contact layer.

Figure 2:
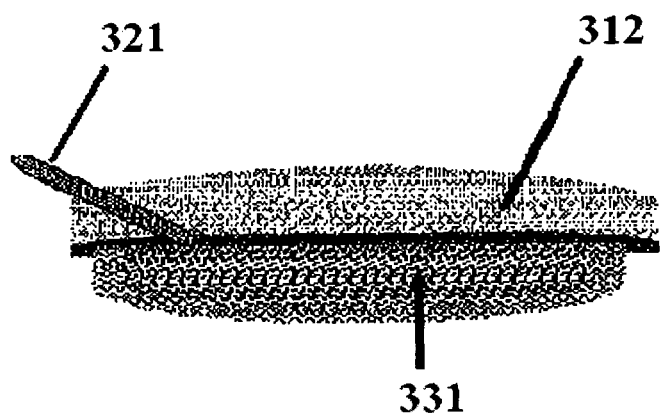
FIG. 2 illustrates a side view of another illustrative embodiment.

As illustrated in FIG. 2, the outer layer of the vacuum sealing layer can be foam layer 312, with the porosity of the foam layer selected retain a portion of the vacuum at the wound site. Foam layer 312 is separated from direct contact with the wound by wound contact layer 331. Vacuum source connector 321 can be slotted through foam layer 312.

The vacuum sealing layer can be, for example, a film layer alone (see FIG. 3, discussed below), or a foam layer alone (see FIG. 2).

A foam layer can be provided by the foam layer of the Versiva® dressing available from ConvaTec (Skillman, N.J.).

The wound contact layer is, for example, a fibrous blend or fibrous material (e.g., non-woven) that forms a cohesive gel when wetted with wound exudate. Such a fibrous material can be provided, for example, by the wound contact layer of the Versiva® dressing (ConvaTec, Skillman, N.J.) or by a fibrous mat of sodium carboxymethylcellulose. A fibrous mat of sodium carboxymethylcellulose is available as AQUACEL® dressing from ConvaTec, as is a similar dressing further including silver. Other exemplary wound contact layers are provided by Medicel™, Carboflex™ (which provides an odor absorbent layer with fibrous material for wicking liquid away from the odor absorbent), Hyalofill™ (forming a hyaluronic acid-rich fibrous gel) or Kaltostat™ (containing alginate) dressings from ConvaTec.

The vacuum sealing layer serves to limit loss of reduced pressure such that a therapeutically useful degree of reduced pressure pertains at the wound site. Loss of reduced pressure (through the vacuum sealing layer) can be significant if compensated by the source of vacuum. It will be recognized the "vacuum" refers to reduced pressure relative to atmospheric pressure. The vacuum source provides a sufficient reduction in pressure such that a therapeutically useful degree of reduced pressure pertains at the wound site.

The wound contact layer can be selected to be effective to adhere the dressing to the wound site, even in the absence of vacuum, and to retain adhesiveness even as it is saturated with exudate liquid. Or, adhesion can be provides at the peripheries of the wound dressing.

Figure 3:
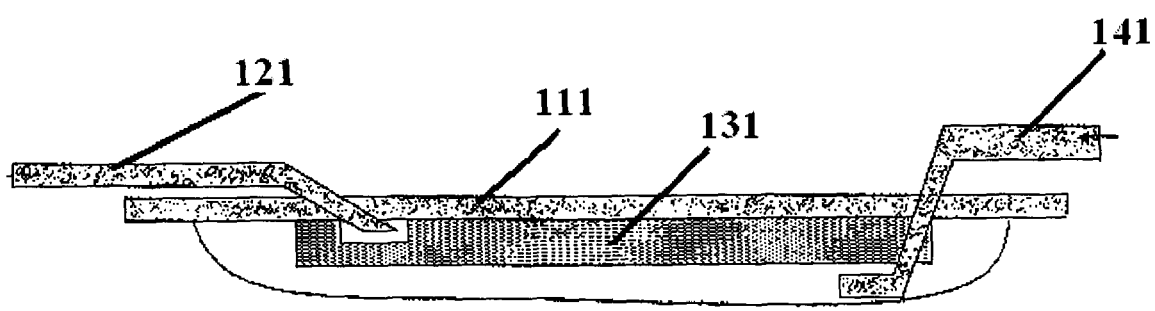
FIG. 3 illustrates a composite of a wound care product similar to that of FIGS. 1a and 1b, but further including a source of irrigation fluid.

As illustrated in FIG. 3, the vacuum wound dressing can be used with a fluid source connector 141 (here illustrated as a tube). The fluid can be, for example, an irrigating fluid, such as saline or a saline substitute, and can include an anti-infective. The irrigating fluid can be pumped to the wound bed, or drawn by the relative vacuum conveyed by vacuum source connector 121 (and sufficiently retained by vacuum sealing layer 111).

In certain embodiments, the wound care dressing(s) used with vacuum provide vacuum sealing layers with maximum pores of greater than 100 micron pore size.

Figure 4:
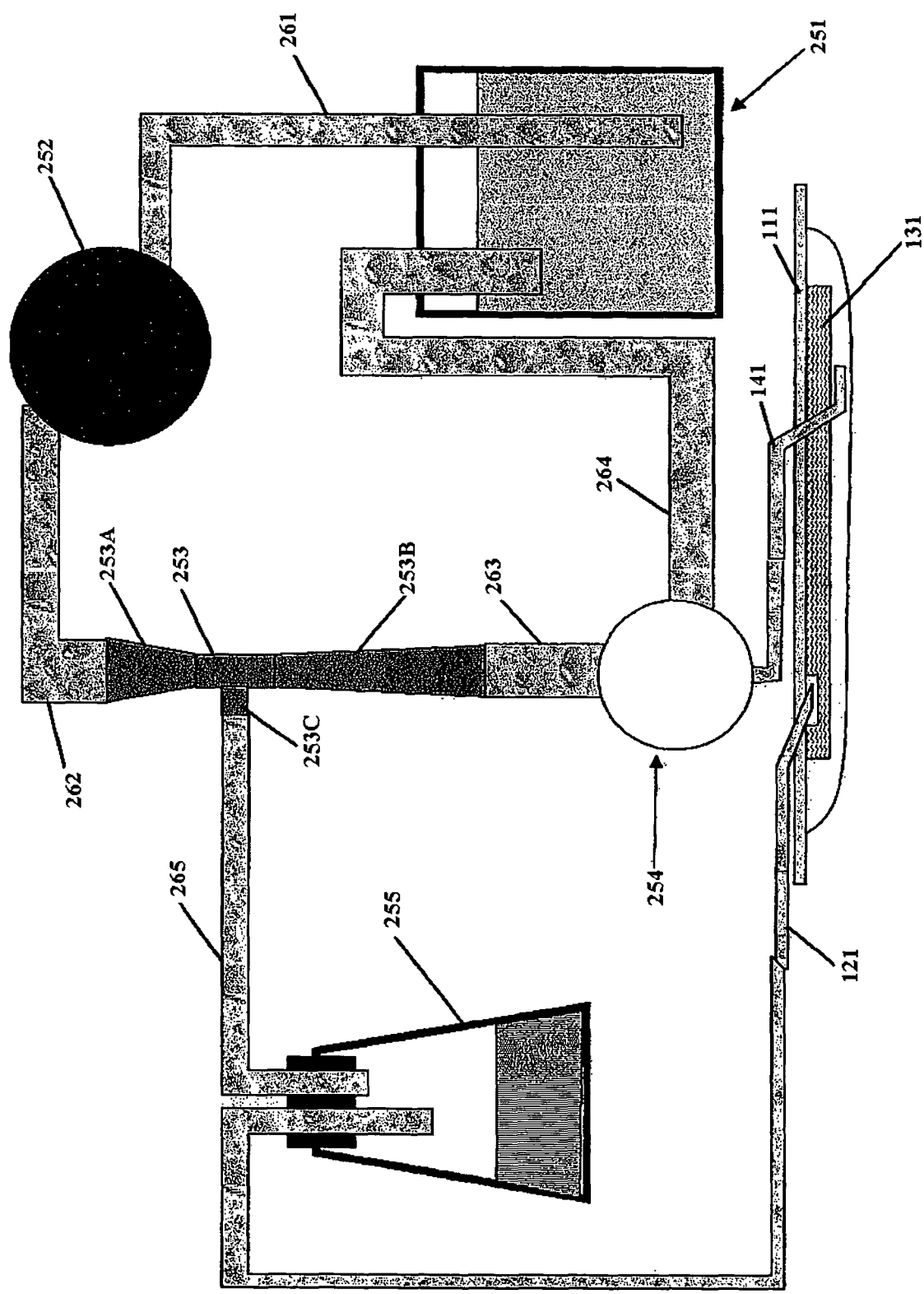
FIG. 4 illustrates a vacuum device for use in wound care.

As illustrated in FIG. 4, a vacuum wound care module can be used to provide vacuum and, optionally, irrigation fluid to a wound. The module can be scaled as a bedside unit, or miniaturized such that it can, for example, be adhered or otherwise affixed near the wound site on a patient. In the illustrated embodiment, there are a reservoir 251, pump module 252, venturi vacuum unit 253, optional diverting valve 254, and trap reservoir 255. Fluid connectors 261, 262, 263, 264 and 265, vacuum source connector 121, and fluid source connector 141 make fluid connections as illustrated. The reservoir 251 provides fluid (i) to move through the venturi vacuum unit 253 to generate vacuum and (ii), optionally, provide irrigating fluid for the wound. If the fluid of the reservoir 251 is to provide irrigating fluid, the fluid is physiological saline or saline substitute suitable for irrigating a wound.

The pump module 252 can be the mechanical pieces that provide pumping, with or without the components that provide motive force or pumping. For example, the pump module 252 can be adapted to couple with a motor to activate the pump parts, or the pump module 252 can be adapted to be engaged by external electromagnet(s) to activate the pump parts. The venturi vacuum unit 253 will typically have a region in which its internal diameter expands to increase the speed of fluid flow (from the inlet 253A to the fluid outlet 253B), thereby reducing pressure according to Bernoulli's Principle and providing vacuum at vacuum outlet 253C.

Optional diverting valve 254 typically has two operating positions, each adapted to allow flow in the "pump circuit" from the reservoir, through the venturi vacuum unit, and returning to the reservoir. One of the operating positions additionally diverts an amount of flow suitable to provide irrigation fluid to the wound. To at least a certain extent, back pressure from the flow pathway to the wound can help regulate the rate of this diverted flow.

Trap reservoir 255 is situated to collect wound exudate and used irrigating fluid before the vacuum draws such spent fluid into the pump circuit. Additional trap reservoirs, and/or sterile filters, can be placed to limit any potential contamination of the pump circuit. The various fluid conduits of the vacuum wound care module can incorporate check valves to help assure that there is no significant flow in an unintended direction. For example, such check valves can prevent flow of reservoir fluid out the vacuum outlet 253C should the pump circuit be temporarily blocked, such as when the diverting valve is switched from one position to the other.

Definitions

The following terms shall have, for the purposes of this application, the respective meanings set forth below.

non-gelling, foam

A non-gelling, foam is a material that does not gel to a functionally significant extent, and is sufficiently porous to move fluid by capillary action.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the text in the Figures.

What is claimed:

1. A vacuum wound care module comprising:
   a fluid reservoir;
   a pump module fluidly connected to the fluid reservoir and adapted for pumping fluid out of the fluid reservoir;
   a venturi vacuum fitting fluidly connected to the pump module and having a vacuum outlet and a fluid outlet;
   a fluid connection from the fluid outlet to the fluid reservoir;
   a trap reservoir fluidly connected to the vacuum outlet; and
   a second fluid connection that is one of:
   (a) fluidly connected to the trap reservoir and (i) adapted to be fitted with a wound dressing to provide vacuum and allow removal of wound exudate or (ii) fitted to such a wound dressing such that, when the wound dressing is employed, it provides vacuum and allows removal of wound exudate, or
   (b) adapted to be fluidly connected to the trap reservoir and fitted to such a wound dressing such that, when the wound dressing is employed, it provides vacuum and allows removal of wound exudate.

2. The vacuum wound care module of claim 1, wherein the second fluid connection is according to (a).

3. The vacuum wound care module of claim 1, wherein the second fluid connection is according to (b).

4. The vacuum wound care module of claim 1, further comprising:
   a diverting valve situated in the first fluid connection, the valve operating between (i) a position that directs fluid from the fluid outlet and the fluid reservoir and (ii) a position that directs a major portion of fluid from the fluid outlet and the fluid reservoir and a minor portion to a third fluid connection; and
   the third fluid connection that is one of
   (A) fluidly connected to the diverting valve and (i) adapted to be fitted with a wound dressing to provide fluid to the wound or (ii) fitted to such a wound dressing such that, when the wound dressing is employed, it provides such fluid, or
   (B) adapted to be fluidly connected to the diverting valve and fitted to such a wound dressing such that, when the wound dressing is employed, it provides such fluid.

5. The vacuum wound care module of claim 4, wherein the third fluid connection is according to (A).

6. The vacuum wound care module of claim 4, wherein the third fluid connection is according to (B).

7. The vacuum wound care module of claim 1, wherein the wound dressing includes a wound contact layer comprising a fibrous blend or fibrous material that forms a cohesive gel when wetted by wound exudate in use.

* * * * *